(12) United States Patent
Gahler et al.

(10) Patent No.: US 11,640,183 B2
(45) Date of Patent: May 2, 2023

(54) FOOT PEDAL CONTROL UNIT

(71) Applicant: D.O.R.C. Dutch Ophthalmic Research Center (International) B.V., Zuidland (NL)

(72) Inventors: Mart Gahler, Zuidland (NL); Wim Rosenquist, Zuidland (NL); John Peter Kuntz, Zuidland (NL)

(73) Assignee: D.O.R.C. Dutch Ophthalmic Research Center (International) B.V., Zuidland (NL)

(*) Notice: Subject to any disclaimer, the term of this patent is extended or adjusted under 35 U.S.C. 154(b) by 0 days.

(21) Appl. No.: 16/830,628

(22) Filed: Mar. 26, 2020

(65) Prior Publication Data

US 2020/0225692 A1 Jul. 16, 2020

Related U.S. Application Data

(63) Continuation of application No. 16/021,599, filed on Jun. 28, 2018, now Pat. No. 10,747,255.

(30) Foreign Application Priority Data

Jun. 29, 2017 (NL) ...................................... 2019147

(51) Int. Cl.
*A61F 9/00* (2006.01)
*G05G 1/30* (2008.04)
(Continued)

(52) U.S. Cl.
CPC .............. *G05G 1/305* (2013.01); *A61F 9/008* (2013.01); *A61F 9/00736* (2013.01); *G05G 1/44* (2013.01);
(Continued)

(58) Field of Classification Search
CPC ....... A61F 9/00736; A61F 9/007; H01H 3/14; H01H 21/26; G03G 1/30; G03G 1/44;
(Continued)

(56) References Cited

U.S. PATENT DOCUMENTS

| 3,841,172 A | 10/1974 | Pilch |
| 5,166,513 A | 11/1992 | Keenan et al. |

(Continued)

FOREIGN PATENT DOCUMENTS

| DE | 7511072 U | 10/1975 |
| EP | 0570765 A2 | 11/1993 |

(Continued)

OTHER PUBLICATIONS

Jun. 7, 2018—Dutch Search Report & WO, NL App No. 2019147.

*Primary Examiner* — Luis A Gonzalez
(74) *Attorney, Agent, or Firm* — Banner & Witcoff, Ltd.

(57) ABSTRACT

The invention relates to a foot pedal control unit for an ophthalmic surgery system. The unit has a base and a treadle that is configured for pivotal pitch movement and for pivotal yaw movement relative to the base for generating control signals to an ophthalmic surgery system. The unit further comprises an inlay cover that is removably placed on the treadle. Optionally, the unit comprises a locking element that is movable between a lock position wherein the treadle is locked against pivotal yaw movement and a release position wherein the treadle is enabled to perform pivotal yaw movement.

20 Claims, 5 Drawing Sheets

(51) Int. Cl.

| | | |
|---|---|---|
| *H01H 3/14* | (2006.01) | |
| *G05G 1/44* | (2008.04) | |
| *A61F 9/007* | (2006.01) | |
| *A61F 9/008* | (2006.01) | |
| *G05G 5/06* | (2006.01) | |
| *G05G 1/483* | (2008.04) | |
| *A61B 17/00* | (2006.01) | |
| *A61B 34/00* | (2016.01) | |

(52) U.S. Cl.
CPC .............. *G05G 1/483* (2013.01); *G05G 5/06* (2013.01); *A61B 34/25* (2016.02); *A61B 2017/00973* (2013.01); *G05G 2505/00* (2013.01)

(58) Field of Classification Search
CPC ............ G03G 1/40; G03G 1/42; G03G 1/483; G05G 5/06; G05G 1/30; G05G 1/44; G05G 1/40; G05G 1/42; G05G 1/483; A61B 34/25; A61B 2017/00973
See application file for complete search history.

(56) References Cited

U.S. PATENT DOCUMENTS

| | | | |
|---|---|---|---|
| 5,199,119 A | 4/1993 | Weber | |
| 5,465,633 A | 11/1995 | Bernloehr | |
| 5,554,894 A | 9/1996 | Sepielli | |
| 5,913,948 A | 6/1999 | Lien | |
| 5,983,749 A | 11/1999 | Holtorf | |
| 6,179,829 B1 | 1/2001 | Bisch et al. | |
| 6,710,237 B2 * | 3/2004 | Adams | G10D 13/11 84/422.1 |
| 6,730,984 B1 | 5/2004 | Ballantine et al. | |
| 7,626,132 B2 | 12/2009 | Mezhinsky | |
| 8,749,188 B2 | 6/2014 | Tran et al. | |
| 9,240,110 B2 | 1/2016 | Roth | |
| 10,180,699 B1 * | 1/2019 | Love | G05G 13/00 |
| 2009/0216189 A1 | 8/2009 | Gasser et al. | |
| 2011/0092887 A1 | 4/2011 | Wong et al. | |
| 2011/0098721 A1 | 4/2011 | Tran et al. | |
| 2011/0106068 A1 | 5/2011 | Horvath et al. | |
| 2014/0364864 A1 | 12/2014 | Lynn et al. | |
| 2018/0253121 A1 * | 9/2018 | Stuart | G05G 1/44 |

FOREIGN PATENT DOCUMENTS

| | | |
|---|---|---|
| GB | 2 138 530 A | 10/1984 |
| GB | 2450626 A | 12/2008 |
| JP | 50-043441 U | 5/1975 |
| JP | 57-157313 U | 10/1982 |
| JP | 2000284846 A | 10/2000 |
| JP | 2000287993 A | 10/2000 |
| WO | 98/08442 A1 | 3/1998 |
| WO | 2003/053294 A2 | 7/2003 |
| WO | 2010/054146 A1 | 5/2010 |
| WO | 2016081700 A1 | 5/2016 |

\* cited by examiner

FOOT PEDAL CONTROL UNIT

CROSS-REFERENCE TO RELATED APPLICATIONS

This application is a continuation of U.S. application Ser. No. 16/021,599 filed Jun. 28, 2018, which claims the benefit of priority under 35 U.S.C. § 119 to Dutch patent application NL 2019147, filed Jun. 29, 2017, each of which prior applications are hereby incorporated by reference in their entireties.

TECHNICAL FIELD

The invention relates to a foot pedal control unit for an ophthalmic surgery system, comprising a base and a treadle that is configured for pivotal pitch movement and for pivotal yaw movement relative to the base for generating control signals to an ophthalmic surgery system, further comprising a locking element that is movable between a lock position wherein the treadle is locked against pivotal yaw movement and a release position wherein the treadle is enabled to perform pivotal yaw movement.

BACKGROUND

Foot pedal control units for generating control signals to an ophthalmic surgery system are generally known in ophthalmic surgery practice. By arranging the treadle to move in pivotal pitch movement, such as an accelerator type pedal, and in pivotal yaw movement, two different parameters can be controlled.

SUMMARY

It is an object of the present invention to provide a foot pedal control unit having an improved user's experience. Thereto, according to the invention, the foot pedal control unit comprises an inlay cover that is removably placed on the treadle.

By providing a removable inlay cover on the treadle, a user of the control unit may customize a personally preferred user interface interaction with the treadle, e.g. in terms of comfort and/or pedal feedback so as to improve the user's experience of the foot pedal control unit.

In a specific embodiment, the foot pedal control unit comprises a carrying handle and a heel support structure on the base, wherein the base is provided with a toe receiving cavity for repositioning the base, the heel support structure and the carrying handle forming an upper bound and a lower bound, respectively, of the toe receiving cavity.

Advantageously, the foot pedal control unit may include a locking element that is movable between a lock position wherein the treadle is locked against pivotal yaw movement and a release position wherein the treadle is enabled to perform pivotal yaw movement. By providing a locking element that blocks and enables pivotal yaw movement upon a user's preference, the dual pivoting functionality can advantageously be temporarily limited to a single pivoting functionality, so that the control unit can also be applied in a situation wherein only a single parameter is to be controlled e.g. when another parameter should be kept constant, thereby obtaining a foot pedal control unit having enhanced functionality.

Preferably, the locking element in the lock position is retracted below a front portion of the treadle and the locking element in the release position extends beyond the front portion of the treadle so that a visible indication of the control unit functionality is provided to the user.

BRIEF DESCRIPTION OF THE DRAWINGS

By way of example only, embodiments of the present invention will now be described with reference to the accompanying figures in which.

It is noted that the figures merely show preferred embodiments according to the invention. In the figures, the same reference numbers refer to equal or corresponding parts.

DETAILED DESCRIPTION

Figure 1A:
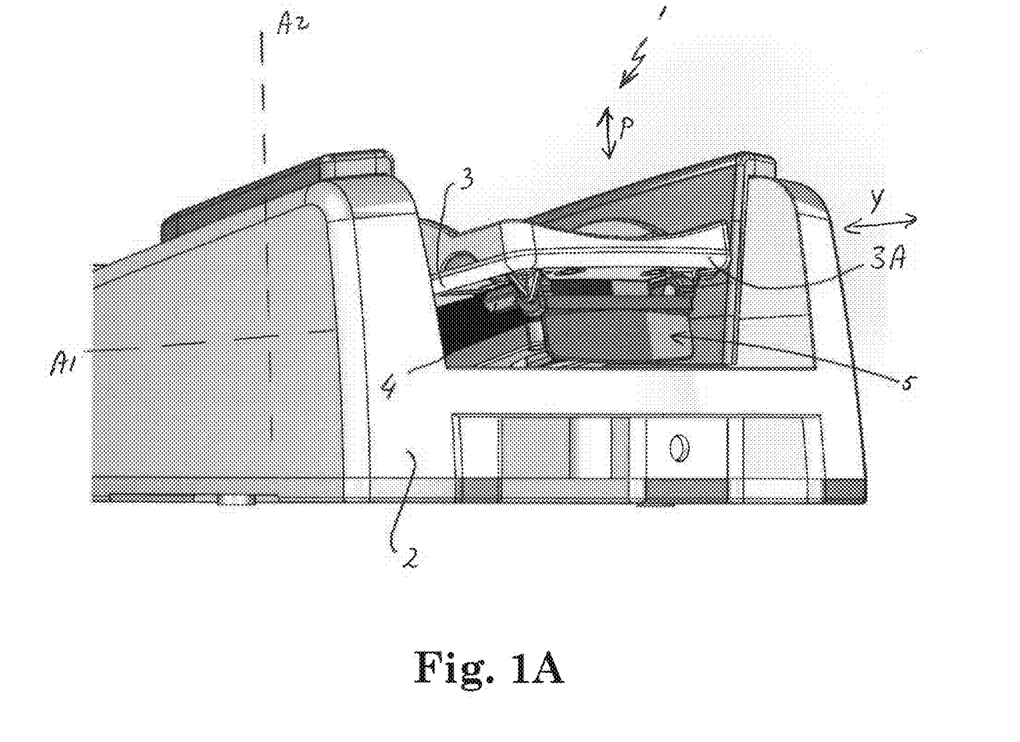
FIG. 1A shows a schematic perspective front view of a foot pedal control unit according to the invention having a locking element in a lock position.

FIG. 1A shows a schematic perspective front view of a foot pedal control unit 1 according to the invention. The foot pedal control unit 1 is arranged for controlling operation of an ophthalmic surgery system such as a vitrectome or a laser unit. The control unit 1 has a base 2 and a treadle 3 that is configured for pivotal pitch movement in a pitch direction P and for pivotal yaw movement in a yaw direction Y relative to the base 2. By moving the treadle 3 in the pivotal pitch direction P, an accelerator type movement is performed, around a pivoting axis Al that is substantially horizontal. Similarly, by moving the treadle 3 in the pivotal yaw direction Y, a pivoting movement to the left or right is performed, around a pivoting axis A2 that is substantially vertical. When a user of the control unit 1 moves the treadle 3 in the pitch direction P and/or the yaw direction Y, a single or multiple number of operational parameters of the controlled ophthalmic surgery system can be adjusted, independently of each other, preferably in a linear way. The treadle 3 can be moved in the pitch direction P and subsequently in the yaw direction Y, or vice versa, or simultaneously. Generally, a movement in the pitch direction P controls a first parameter while a movement in the yaw direction Y controls a second parameter, thus providing a dual linear functionality on the control unit or foot switch. However, in principle, a multiple number of parameters can be controlled by moving the treadle 3 in the pitch or yaw direction.

The foot pedal control unit 1 has a locking element that is movable between a lock position and a release position. When the locking element is in the lock position, the treadle 3 is locked against pivotal yaw movement. Further, when the locking element is in the release position, the treadle 3 is enabled to perform pivotal yaw movement. When the locking element is in the release position, the foot pedal control unit 1 is arranged for generating, depending on a yaw position of the treadle 3, a control signal controlling the second parameter. Preferably, an alert signal is transmitted to the ophthalmic surgery system when the locking element is brought into the release position so that the ophthalmic surgery system adjust the second parameter in conformity with the control signal controlling said second parameter. The locking element includes a lever 4 that is pivotable between a retracted position and an extended position corresponding to the lock and release position, respectively, of the locking element. In FIG. 1A the lever 4 is in the retracted position wherein the lever 4 is retracted below a front portion 3A of the treadle 3, thereby providing a visible indication that the treadle 3 can not move in the pivotal yaw direction Y.

Figure 1B:
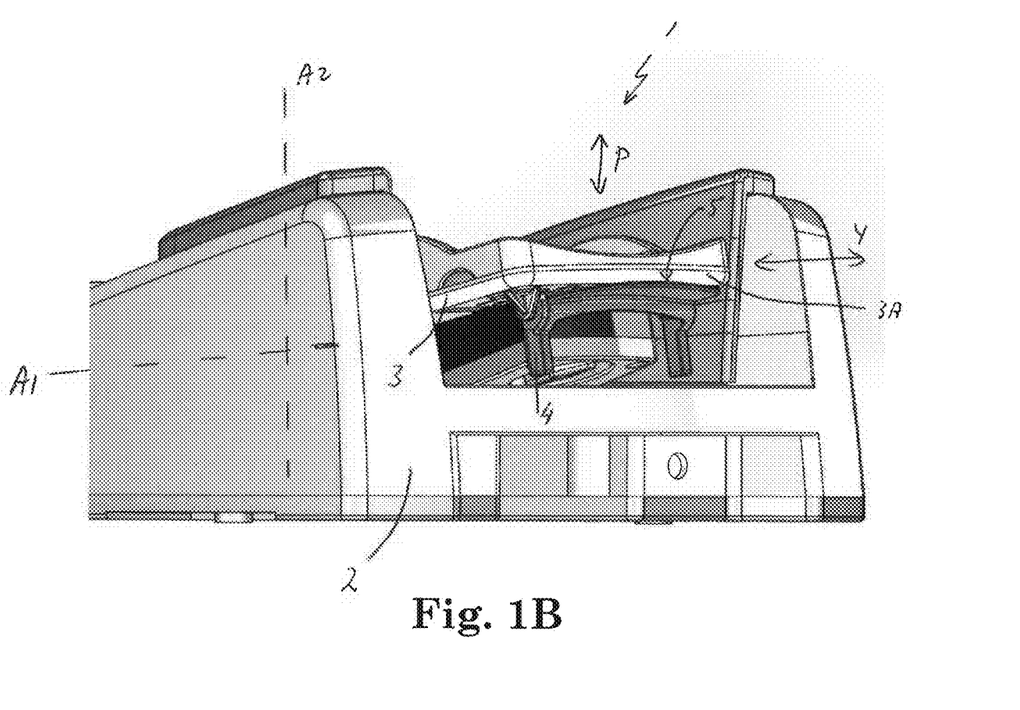
FIG. 1B shows a schematic perspective front view of the foot pedal control unit of FIG. 1A wherein the locking element is in a release position.

FIG. 1B shows a schematic perspective front view of the foot pedal control unit 1 wherein the lever 4 is in the extended position wherein the lever 4 extends beyond the front portion 3A of the treadle 3, thereby providing a visible indication the treadle 3 can move in the pivotal yaw direction Y.

Figure 1C:
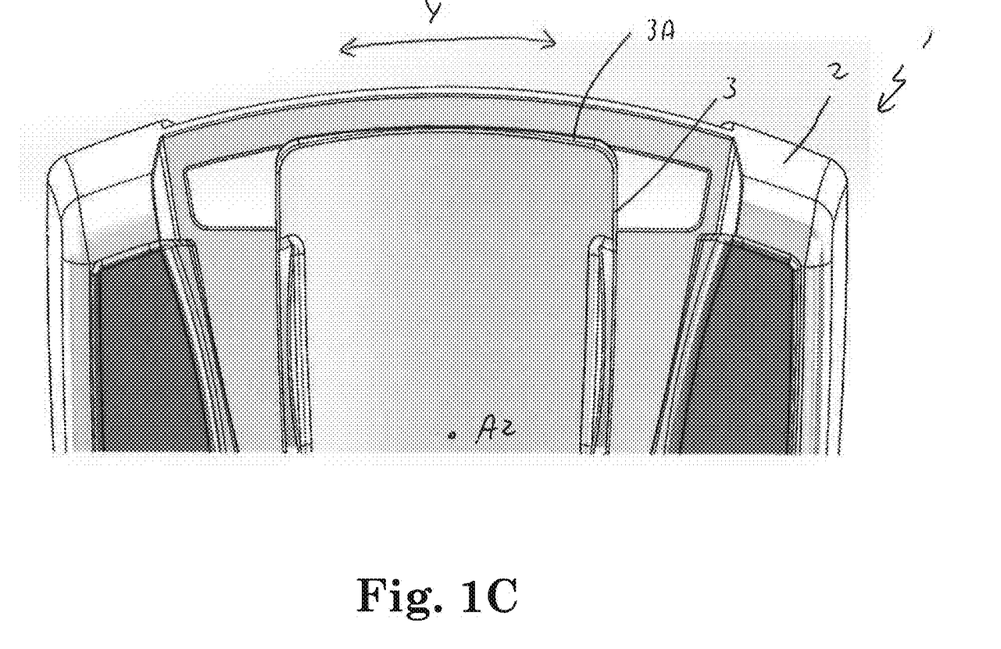
FIG. 1C shows a schematic partial top view of a foot pedal control unit of FIG. 1A wherein the locking element is in the lock position.
Figure 1D:
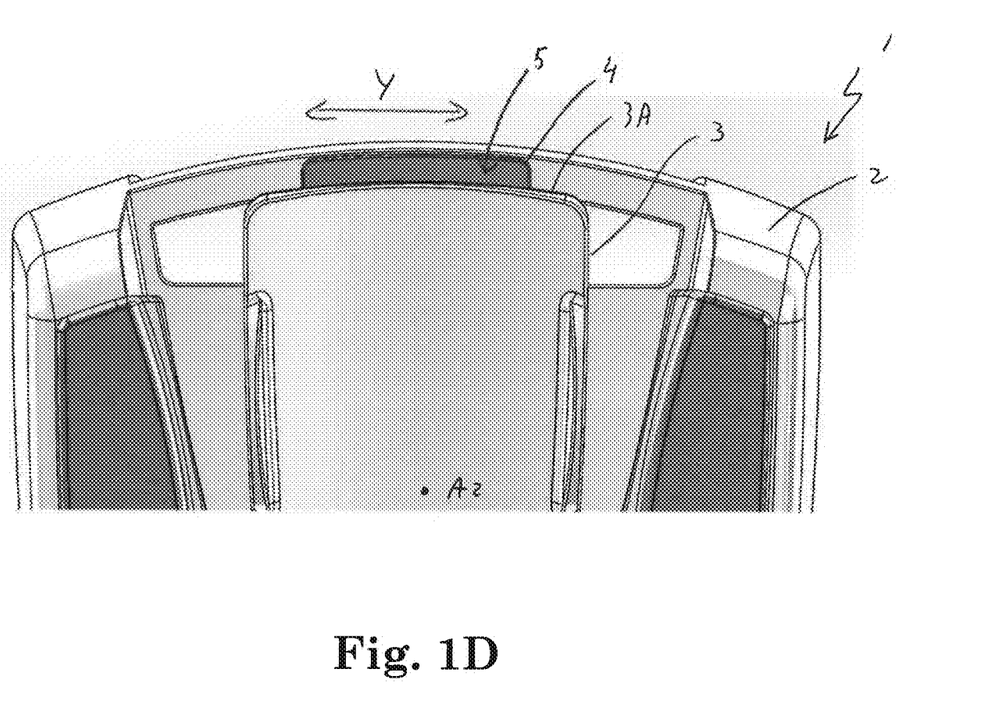
FIG. 1D shows a schematic partial top view of a foot pedal control unit of FIG. 1A wherein the locking element is in the release position.

FIGS. 1C and 1D show a schematic partial top views of the foot pedal control unit 1. In FIG. 1C the locking element is in the lock position, wherein the lever 4 is in the retracted position, below the treadle 3, while in FIG. 1D the locking element is in the release position, wherein the lever 4 is in the extended position extending beyond the treadle 3.

Advantageously, the locking element has an upper surface 5, on an extended portion of the lever 4 that is visible when the lever is in its extended position. Said upper surface 5 is provided with an optic marker, in the shown embodiment designed as a specific colour, e.g. green, to enhance a visibility of the indication that the treadle can move in the pivotal yaw direction Y. In the shown embodiment, the complete lever 4 is coloured, however the lever 4 may also partially be coloured. Apparently, the optic marker may have another colour and/or may extend across a portion or the entire extended upper surface 5 of the lever 4. Further, the optic marker may have a specific shape such as a bar or disc.

It is noted that, in principle, the lever 4 may be designed to work the other way around, i.e. that in its retracted position the treadle 3 is enable to perform pivotal yaw movement while in its extended position the treadle 3 is locked against pivotal yaw movement. Then, the optic marker on the upper surface 5 may have another colour, e.g. red. Further, the lever 4 may be positioned at another location on the base 2, e.g. near a back portion of the base 2, opposite to the front portion of the base 2.

In another embodiment, the locking element is implemented in another way, e.g. including a bar that is movable along a linear trajectory. The locking element may be operable by a foot of the user and/or by an actuator that is electronically controlled.

Figure 2A:
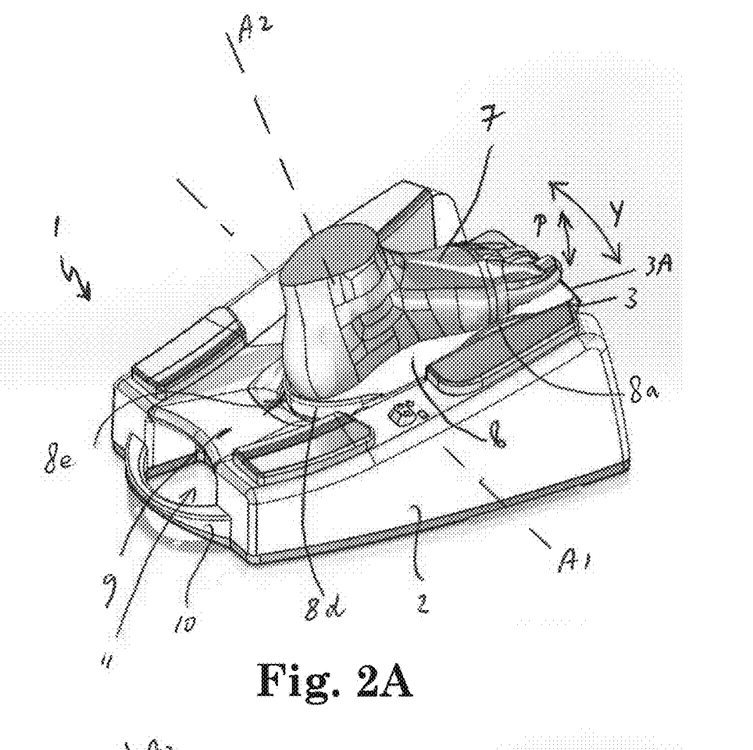
FIG. 2A shows a schematic perspective top view of the foot pedal control unit of FIG. 1A provided with an inlay cover.

FIG. 2A shows a schematic perspective top view of the foot pedal control unit 1 provided with an inlay cover 8 that is removably placed on the treadle 3. In the embodiment shown in FIG. 2A the inlay cover 8 is provided with upwardly raising side flanges 8a, a' at the side edges 8b, 8c of the cover 8, as illustrated in more detail in FIG. 3, in order to provide additional support for dual linear motion of the treadle 3, especially for movement in the pivotal yaw direction Y. Further, the inlay cover 8 includes upwardly raising flange 8d, also called heelcup, at a rear side 8e of the cover 8, for providing support for a user's foot 7 that is fully placed on the inlay cover 8. In principle, the inlay cover 8 may be provided with either the side flanges 8a, a' or the rear flange 8d. Further, the inlay cover 8 may be implemented without the above described upwardly raising flanges.

Figure 2B:
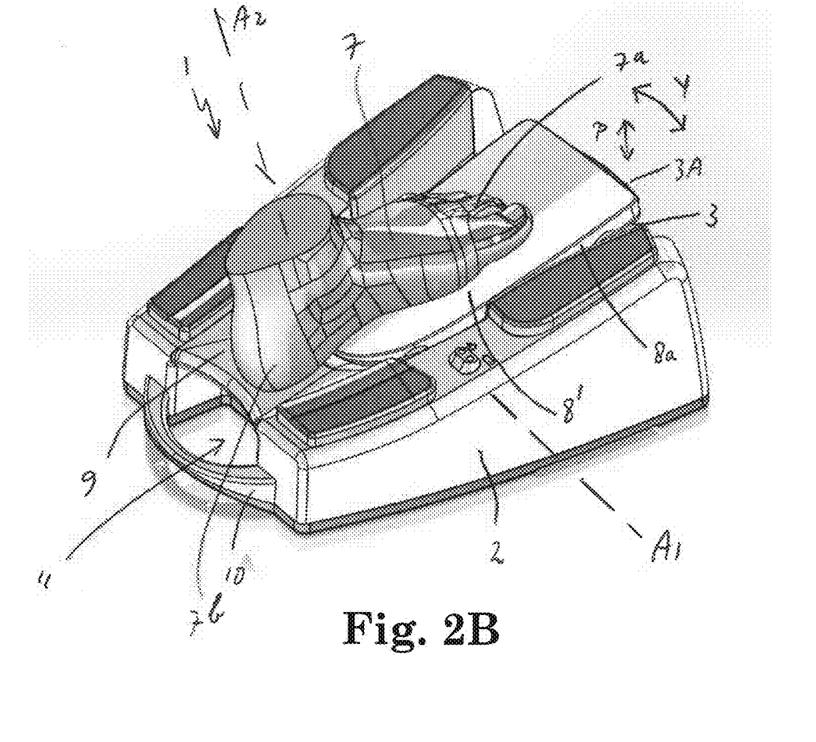
FIG. 2B shows a schematic perspective top view of the foot pedal control unit of FIG. 1A provided with another inlay cover.

FIG. 2B shows a schematic perspective top view of the foot pedal control unit 1 provided with another inlay cover 8'. Here, the inlay cover 8' is provided with side flanges 8a, a' that extend downwardly, towards the treadle 3, without a rear flange 8d. The user's foot 7 is placed such that the toes 7a are located on the inlay cover 8' while the heel 7b rests on a heel support structure 9 that is rigidly connected or integrally formed with the base 2. In another embodiment of the foot pedal control unit 1 no such heel support structure 9 is provided.

In the embodiments shown in FIGS. 2A and 2B the inlay cover 8, 8' is removable so as to offer a user the possibility to adopt experienced operation of the treadle 3 to personal preferences. The inlay cover 8, 8' is preferably made from comfortable and/or biocompatible material such as a rubber.

Figure 3:
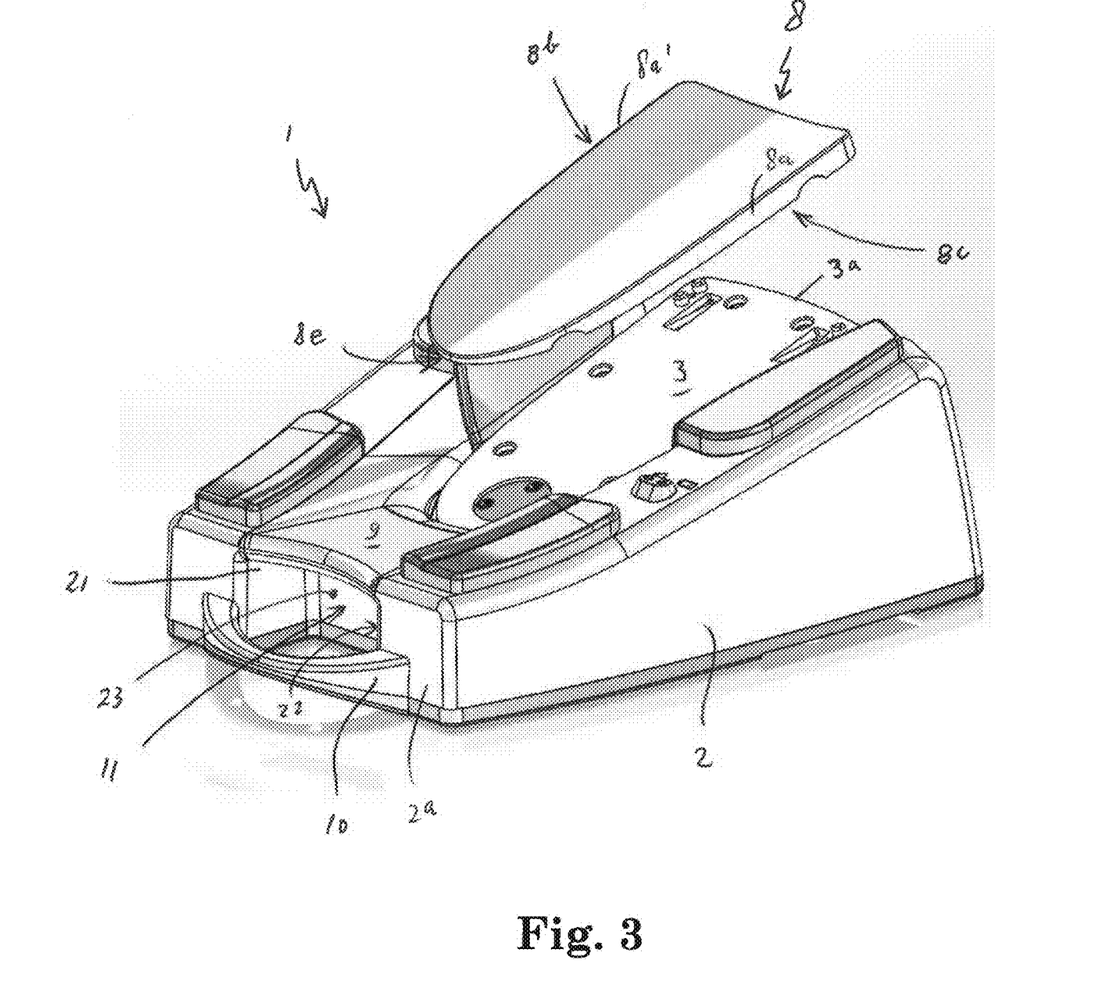
FIG. 3 shows a schematic perspective top view of the foot pedal control unit of FIG. 2B wherein the inlay cover is being removed.

FIG. 3 shows a schematic perspective top view of the foot pedal control unit 1 wherein the inlay cover 8' shown in FIG. 2B is being removed. Here, the inlay cover 8' is pulled upwardly from the treadle 3 so that another type of inlay cover can be placed on the treadle 3. Generally, the inlay cover 8 may be shaped such that it fits seamless on the treadle 3, e.g. by providing downwardly extending flanges 8a, a'. Further, removable connection elements can be applied such as a fastener.

In use, the foot pedal control unit 1 typically is provided with an inlay cover 8, and one or more additional inlay covers 8' that are removably placed on the treadle 3. The control unit 1 may further include one or more additional inlay covers 8' that may each removably replace the inlay cover 8 that is placed on the treadle 3 so as to personalize the control unit 1, e.g. for optimizing comfort and/or individual preferences of specific users of the control unit 1. Then, the inlay cover 8 on the treadle and the one or more additional inlay covers 8' form a multiple number of inlay covers 8, 8', instead of a single inlay cover removably placed on the treadle, each of the inlay covers 8, 8' being removably placeable on the treadle 3. Further, each of the inlay covers 8, 8' may be customized, e.g. in terms of appearance, size, material, compressibility and/or support profile, thereby personalizing the inlay covers for their individual users.

The foot pedal control unit 1 further comprises a carrying handle 10 for manually carrying the unit 1. The handle 10 is located at a rear side 2a on the base 2, below a height level of the heel support structure 9. The heel support structure 9 and the carrying handle 10 may form an upper bound and a lower bound, respectively, of a toe receiving cavity 11 formed in the base 2 for repositioning the base 2 on the floor or other support structure on which the control unit is located.

By inserting a toe or toes into said cavity 11 and by controllably exerting a force to the base 2 in a desired moving direction, the base 2 can be easily repositioned.

Preferably, the cavity 11 is formed at the rear side 2a of the base 2, the cavity 11 being located below the heel support structure 9. As shown in FIG. 3, the cavity may be bounded at its top side at least partly by the heel support structure 9, at its left side at least partly by a left side wall structure 21, and at its right side at least partly by a right side wall structure 22, both side wall structures 21, 22 extending from the height level of the carrying handle 10 upwardly to the heel support structure 9 for receiving a force exerted by a toe or toes moving the base 2 sidewardly. Further, the cavity 11 may be bounded at its front side at least partly by a front wall structure 23 formed as a wall portion that is corrugated relative to the rear side 2a of the base 2 and extends upwardly to the heel support structure 9 serving as a structure for receiving a force exerted by a toe or toes moving the base 2 forwardly. The carrying handle 10 may form a bottom boundary structure of cavity 11, below the heel support structure 9. The carrying handle 10 may also extend beyond said heel support structure 9, in the rear side direction, as shown in FIG. 3, thus enabling a user to insert a toe or toes in a volume between the carrying handle 10 and the heel support structure 9, and to exert a rearwardly directed force, by said toe or toes, on said carrying handle 10 for moving the base 2 backwardly.

Figure 4:
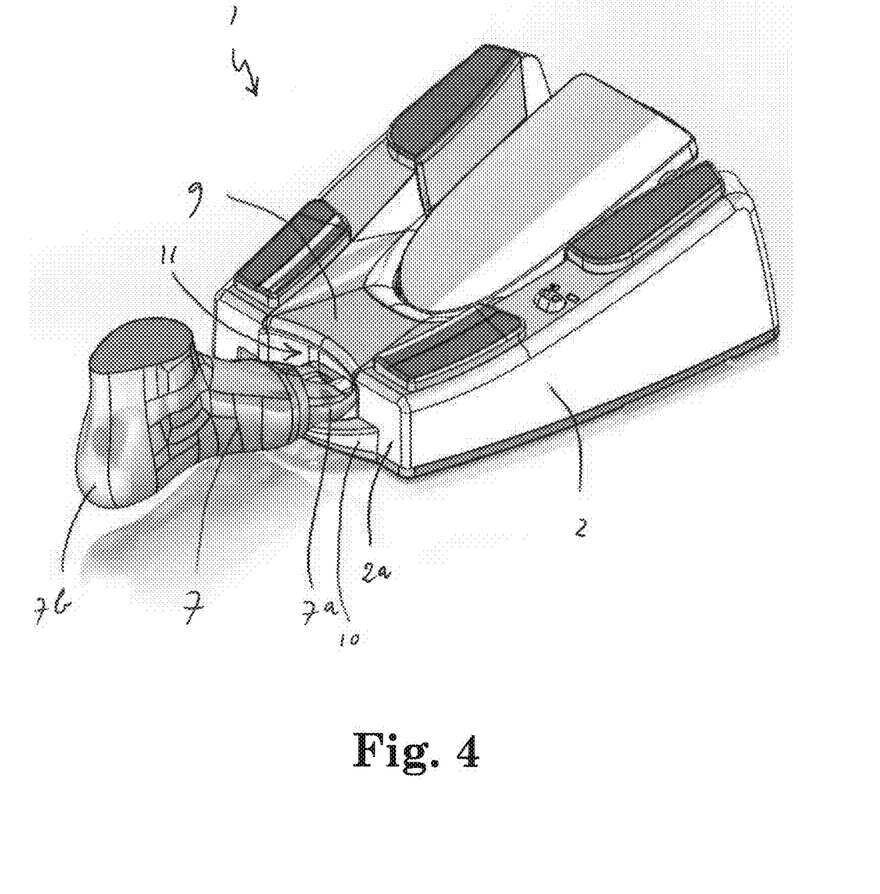
FIG. 4 shows a schematic perspective top view of the foot pedal control unit of FIG. 1A being repositioned by a user's foot.

FIG. 4 shows a schematic perspective top view of the foot pedal control unit 1 being repositioned by a user's foot 7. Here, the toe receiving cavity 11 receives toes 7a of the user's foot 7. Then, the carrying handle 10 may serve as a toe bar for easily moving the base 1 forwardly, backwardly or sidewardly. Then, accidental activation of buttons or other controlling elements on the control unit 1 is counteracted.

It is noted that the toe receiving cavity for repositioning the base can not only be applied to a foot pedal control unit as defined in claim 1, but more generally also to a foot pedal control unit for an ophthalmic surgery system, comprising a base and a treadle that is configured for pivotal movement relative to the base for generating control signals to an ophthalmic surgery system, such as a accelerator type foot pedal control unit wherein the treadle is permanently blocked against yaw movement.

It is further noted that the locking element that is movable between a lock position wherein the treadle is locked against pivotal yaw movement and a release position wherein the treadle is enabled to perform pivotal yaw movement can not only be applied to a foot pedal control unit as defined in claim 1, but more generally also to a foot pedal control unit for an ophthalmic surgery system, comprising a base and a treadle that is configured for pivotal movement relative to the base for generating control signals to an ophthalmic surgery system.

The invention is not restricted to the embodiments described above. It will be understood that many variants are possible.

These and other embodiments will be apparent for the person skilled in the art and are considered to fall within the scope of the invention as defined in the following claims. For the purpose of clarity and a concise description features are described herein as part of the same or separate embodiments. However, it will be appreciated that the scope of the invention may include embodiments having combinations of all or some of the features described.

The invention claimed is:

1. A foot pedal control unit for an ophthalmic surgery system, comprising a base and a treadle that is configured for pivotal pitch movement and for pivotal yaw movement relative to the base for generating control signals to an ophthalmic surgery system, the foot pedal control unit further comprising a multiple number of inlay covers, wherein one of said multiple number of inlay covers is removably placed on the treadle and covers the treadle, wherein one or more others of said multiple number of inlay covers are configured for removably covering the treadle,
    wherein each of said multiple number of inlay covers is different from one another, is configured for separate, user-selective connection to the treadle, and has a surface for supporting and underlying at least toes of a user thereon, and
    wherein one or more of said multiple number of inlay covers includes an upwardly rising flange at a rear edge of said one or more inlay covers and/or an upwardly rising flange at a side edge of said one or more inlay covers.

2. The foot pedal control unit of claim 1, wherein the multiple number of inlay covers are customized in terms of appearance, size, material, compressibility and/or support profile.

3. The foot pedal control unit of claim 1, wherein each of said multiple number of inlay covers is shaped such that it fits seamlessly on the treadle.

4. The foot pedal control unit of claim 1, wherein the foot pedal control unit further comprises a heel support structure that is rigidly connected to, or integrally formed with, the base.

5. The foot pedal control unit of claim 1, wherein the foot pedal control unit further comprises a carrying handle connected to a rear side of the base.

6. The foot pedal control unit of claim 4, wherein the base is provided with a toe receiving cavity, located at the rear side of the base, for repositioning the base, wherein the heel support structure forms an upper bound of the toe receiving cavity.

7. The foot pedal control unit of claim 6, wherein the toe receiving cavity is bounded at its left and right side at least partly by a left side wall structure and a right side wall structure, respectively, both of said right side wall structure and said left side wall structure extending from a height level of the carrying handle upwardly to the heel support structure.

8. The foot pedal control unit of claim 6, wherein the toe receiving cavity is bounded at its front side at least partly by a front wall structure, formed as a wall portion that is corrugated relative to the rear side of the base and extends upwardly to the heel support structure.

9. A foot pedal control unit for an ophthalmic surgery system comprising a base and a treadle that is configured for pivotal pitch movement and for pivotal yaw movement relative to the base for generating control signals to an ophthalmic surgery system, the foot pedal control unit further comprising a multiple number of inlay covers, wherein one of said multiple number of inlay covers is removably placed on the treadle and covers the treadle, wherein one or more others of said multiple number of inlay covers are configured for removably covering the treadle,
    wherein each of said multiple number of inlay covers is different from one other is configured for separate, user-selective connection to the treadle, and has a surface for supporting and underlying at least toes of a user thereon,
said foot pedal control unit further comprising a heel support structure that is rigidly connected to, or integrally formed with, the base, and
    a carrying handle connected to a rear side of the base,
    wherein the base is provided with a toe receiving cavity, located at the rear side of the base, for repositioning the base,
    wherein the heel support structure forms an upper bound of the toe receiving cavity and the carrying handle forms a bottom boundary structure of the toe receiving cavity, the carrying handle extending beyond the heel support structure, in a rear side direction, enabling one or more of the toes the user to exert a rearwardly directed force on said carrying handle for moving the base rearwardly.

10. The foot pedal control unit of claim 9, wherein the multiple number of inlay covers each include an upwardly rising flange at a rear edge of each cover and/or an upwardly rising flange at a side edge of each cover.

11. The foot pedal control unit claim 9, wherein the toe receiving cavity is bounded at its left and right side at least partly by a left side wall structure and a right side wall structure, respectively, both of said right side wall structure and said left side wall structure extending from a height level of the carrying handle upwardly to the heel support structure.

12. The foot pedal control unit of claim 9, wherein the toe receiving cavity is bounded at its front side at least partly by a front wall structure, formed as a wall portion that is corrugated relative to the rear side of the base and extends upwardly to the heel support structure.

13. The foot pedal control unit of claim 9, wherein each of said multiple number of inlay covers is shaped such that it fits seamlessly on the treadle.

14. A method for customizing a foot pedal control unit for an ophthalmic surgery system, wherein the foot pedal control unit comprises a base and a treadle that is configured for pivotal pitch movement and for pivotal yaw movement relative to the base for generating control signals to an ophthalmic surgery system, the method comprising the steps of: removing a first inlay cover from the treadle of the foot pedal control unit, and subsequently, after removing the first inlay cover, covering the treadle with a second inlay cover, wherein said first inlay cover is different from said second inlay cover and each of said first and second inlay covers is configured for separate, user-selective connection to the treadle, and has a surface for supporting and underlying at least toes of a user thereon, wherein a multiple of inlay covers, including said first inlay cover and said second inlay cover, are different from one another, are configured for removably covering the treadle, and have a surface for supporting and underlying at least toes of a user thereon, and wherein one or more of said multiple number of inlay covers includes an upwardly rising flange at a rear edge of said one or more inlay covers and/or an upwardly rising flange at a side edge of said one or more inlay covers.

15. The method claim 14, wherein the multiple number of inlay covers are customized in terms of appearance, size, material, compressibility and/or support profile.

16. The method of claim 14, wherein the foot pedal control unit further comprises a heel support structure that is rigidly connected to, or integrally formed with, the base.

17. The method of claim 16, wherein the foot pedal control unit further comprises a carrying handle connected to a rear side of the base.

18. The method of claim 17, wherein the base is provided with a toe receiving cavity, located at the rear side of the base, for repositioning the base, wherein the heel support structure forms an upper bound of the toe receiving cavity.

19. The method of claim 18, wherein the toe receiving cavity is bounded at its left and right side at least partly by a left side wall structure and a right side wall structure, respectively, both of said right side wall structure and said left side wall structure extending from a height level of the carrying handle upwardly to the heel support structure.

20. The method of claim 18, wherein the toe receiving cavity is bounded at its front side at least partly by a front wall structure, formed as a wall portion that is corrugated relative to the rear side of the base and extends upwardly to the heel support structure.

* * * * *